(12) United States Patent
Efremova et al.

(10) Patent No.: US 7,640,637 B2
(45) Date of Patent: Jan. 5, 2010

(54) METHODS TO MODIFY THE FIBROUS LANDING LAYER OF A FOAM BASED FASTENER AND PRODUCTS MADE FROM THE SAME

(75) Inventors: Nadezhda V. Efremova, Neenah, WI (US); Lisha Yu, Appleton, WI (US); Eric Steindorf, Roswell, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 445 days.

(21) Appl. No.: 11/264,818

(22) Filed: Nov. 1, 2005

(65) Prior Publication Data

US 2007/0119032 A1 May 31, 2007

(51) Int. Cl.
*B32B 3/02* (2006.01)
*B32B 33/00* (2006.01)
*A44B 18/00* (2006.01)
*B32B 3/00* (2006.01)

(52) U.S. Cl. .............. 24/442; 428/85; 428/91; 428/99; 428/192; 28/161

(58) Field of Classification Search ........... 24/442–452; 28/159, 161, 162, 165, 166; 162/109, 113, 162/116; 428/85, 91, 95, 99, 100, 192; 442/361, 442/364, 365; 451/28
See application file for complete search history.

(56) References Cited

U.S. PATENT DOCUMENTS

| | | |
|---|---|---|
| 458,725 A | 9/1891 | Forrester |
| 2,787,241 A | 4/1957 | Kelley |
| 3,093,600 A | 6/1963 | Spencer et al. |
| 3,171,820 A | 3/1965 | Volz et al. |
| 3,214,816 A | 11/1965 | Mathison |
| 3,266,927 A | 8/1966 | Lorenz et al. |
| 3,338,992 A | 8/1967 | Kinney |
| 3,341,394 A | 9/1967 | Kinney |
| 3,397,697 A | 8/1968 | Rickard |
| 3,485,706 A | 12/1969 | Evans |
| 3,502,763 A | 3/1970 | Hartmann |
| 3,542,615 A | 11/1970 | Dobo et al. |
| 3,661,674 A | 5/1972 | Higgs et al. |

(Continued)

FOREIGN PATENT DOCUMENTS

CA          1188101          6/1985

(Continued)

OTHER PUBLICATIONS

U.S. Appl. No. 10/956,613, Fung-jou Chen et al., entitled Foam-Based Fastners, Filed Sep. 30, 2004.

*Primary Examiner*—Robert J Sandy
(74) *Attorney, Agent, or Firm*—Dority & Manning, P.A.

(57) ABSTRACT

Methods to modify an engaging surface of a fibrous landing layer of a mechanical fastener are generally disclosed, along with products made from the same. For instance, the engaging surface of the landing layer can be mechanically modified to increase the fuzziness of the layer, which allows more fibers to engage the other surface of the mechanical fastener. For example, the improved engaging surface of the landing layer can increase the shear resistance of a mechanical fastener comprising a foam layer and a landing layer.

8 Claims, 11 Drawing Sheets

U.S. PATENT DOCUMENTS

| | | |
|---|---|---|
| 3,692,618 A | 9/1972 | Dorschner et al. |
| 3,708,382 A | 1/1973 | Erb |
| 3,708,833 A | 1/1973 | Ribich et al. |
| 3,802,817 A | 4/1974 | Matsuki et al. |
| 3,849,241 A | 11/1974 | Butin et al. |
| 3,922,455 A | 11/1975 | Brumlik |
| 4,062,915 A | 12/1977 | Stricharczuk et al. |
| 4,100,324 A | 7/1978 | Anderson et al. |
| 4,183,984 A | 1/1980 | Browers et al. |
| 4,216,257 A | 8/1980 | Schams et al. |
| 4,285,343 A | 8/1981 | McNair |
| 4,340,563 A | 7/1982 | Appel et al. |
| 4,366,804 A | 1/1983 | Abe |
| 4,443,513 A | 4/1984 | Meitner et al. |
| 4,540,717 A | 9/1985 | Mahnke et al. |
| RE32,026 E | 11/1985 | Yamashita et al. |
| 4,556,146 A | 12/1985 | Swanson et al. |
| 4,589,876 A | 5/1986 | Van Tilburg |
| 4,608,047 A | 8/1986 | Mattingly |
| 4,631,077 A | 12/1986 | Spicer et al. |
| 4,649,895 A | 3/1987 | Yasuki et al. |
| 4,652,487 A | 3/1987 | Morman |
| 4,655,760 A | 4/1987 | Morman et al. |
| 4,656,196 A | 4/1987 | Kelly et al. |
| 4,657,802 A | 4/1987 | Morman |
| 4,666,948 A | 5/1987 | Woerner et al. |
| 4,687,478 A | 8/1987 | Van Tilburg |
| 4,707,398 A | 11/1987 | Boggs |
| 4,720,415 A | 1/1988 | Vander Wielen et al. |
| 4,741,949 A | 5/1988 | Morman et al. |
| 4,753,649 A | 6/1988 | Pazdernik |
| 4,781,966 A | 11/1988 | Taylor |
| 4,789,699 A | 12/1988 | Kieffer et al. |
| 4,805,275 A | 2/1989 | Suzuki et al. |
| 4,818,464 A | 4/1989 | Lau |
| 4,834,739 A | 5/1989 | Linker, III et al. |
| 4,881,997 A | 11/1989 | Hatch et al. |
| 4,894,060 A | 1/1990 | Nestegard et al. |
| 4,906,263 A | 3/1990 | Von Blucher et al. |
| 4,917,697 A | 4/1990 | Osborn, III et al. |
| 4,965,122 A | 10/1990 | Morman |
| 4,981,747 A | 1/1991 | Morman |
| 4,984,339 A | 1/1991 | Provost et al. |
| 5,005,242 A | 4/1991 | Kennedy et al. |
| 5,011,480 A | 4/1991 | Gossens et al. |
| 5,046,479 A | 9/1991 | Usui |
| 5,053,028 A | 10/1991 | Zoia et al. |
| 5,058,247 A | 10/1991 | Thomas et al. |
| 5,094,559 A | 3/1992 | Rivera et al. |
| 5,100,400 A | 3/1992 | Mody et al. |
| 5,110,649 A | 5/1992 | Morse et al. |
| 5,114,781 A | 5/1992 | Morman |
| 5,226,992 A | 7/1993 | Morman |
| 5,234,969 A | 8/1993 | Clark et al. |
| 5,242,436 A | 9/1993 | Weil et al. |
| 5,244,482 A | 9/1993 | Hassenboehler, Jr. et al. |
| 5,284,703 A | 2/1994 | Everhart et al. |
| 5,336,545 A | 8/1994 | Morman |
| 5,369,858 A | 12/1994 | Gilmore et al. |
| H1420 H | 2/1995 | Richardson |
| 5,389,202 A | 2/1995 | Everhart et al. |
| 5,397,316 A | 3/1995 | LaVon et al. |
| 5,399,219 A | 3/1995 | Roessler et al. |
| 5,413,853 A | 5/1995 | Imashiro et al. |
| 5,419,015 A | 5/1995 | Garcia et al. |
| 5,436,278 A | 7/1995 | Imashiro et al. |
| 5,482,755 A | 1/1996 | Manning |
| 5,518,795 A | 5/1996 | Kennedy et al. |
| 5,520,980 A | 5/1996 | Morgan et al. |
| 5,611,789 A | 3/1997 | Seth et al. |
| 5,614,281 A | 3/1997 | Jackson et al. |
| 5,622,578 A | 4/1997 | Thomas |
| 5,670,101 A | 9/1997 | Nathoo et al. |
| 5,676,652 A | 10/1997 | Hunter et al. |
| 5,681,303 A | 10/1997 | Mills et al. |
| 5,720,740 A | 2/1998 | Thomas |
| 5,728,057 A | 3/1998 | Ouellette et al. |
| 5,728,058 A | 3/1998 | Ouellette et al. |
| 5,728,146 A | 3/1998 | Burkett et al. |
| 5,735,889 A | 4/1998 | Burkett et al. |
| 5,741,318 A | 4/1998 | Ouellette et al. |
| 5,763,044 A | 6/1998 | Ahr et al. |
| 5,782,819 A | 7/1998 | Tanzer et al. |
| 5,817,704 A | 10/1998 | Shiveley et al. |
| 5,827,393 A | 10/1998 | Kinzelmann et al. |
| 5,837,005 A | 11/1998 | Viltro et al. |
| 5,858,515 A | 1/1999 | Stokes et al. |
| 5,860,945 A | 1/1999 | Cramer et al. |
| 5,904,710 A | 5/1999 | Davis et al. |
| 5,906,637 A | 5/1999 | Davis et al. |
| 5,925,072 A | 7/1999 | Davis et al. |
| 5,968,027 A | 10/1999 | Cole et al. |
| 5,979,024 A | 11/1999 | Renwick |
| 5,980,562 A | 11/1999 | Ouellette et al. |
| 6,019,782 A | 2/2000 | Davis et al. |
| 6,024,761 A | 2/2000 | Barone et al. |
| 6,048,326 A | 4/2000 | Davis et al. |
| 6,063,067 A | 5/2000 | Takizawa et al. |
| 6,074,413 A | 6/2000 | Davis et al. |
| 6,096,067 A | 8/2000 | Cramer et al. |
| 6,102,937 A | 8/2000 | Cramer et al. |
| 6,123,717 A | 9/2000 | Davis et al. |
| 6,133,332 A | 10/2000 | Ide et al. |
| 6,205,623 B1 | 3/2001 | Shepard et al. |
| 6,224,364 B1 | 5/2001 | Harvey |
| 6,245,697 B1 | 6/2001 | Conrad et al. |
| 6,248,419 B1 | 6/2001 | Kennedy et al. |
| 6,306,234 B1 | 10/2001 | Barker et al. |
| 6,314,627 B1 | 11/2001 | Ngai et al. |
| 6,336,935 B1 | 1/2002 | Davis et al. |
| 6,343,410 B2 | 2/2002 | Greenway et al. |
| 6,406,466 B1 | 6/2002 | Pozniak et al. |
| 6,436,020 B1 | 8/2002 | Weingand |
| 6,443,525 B1 | 9/2002 | Haupt |
| 6,501,002 B1 | 12/2002 | Roe et al. |
| 6,503,615 B1 | 1/2003 | Horii et al. |
| 6,516,502 B1 | 2/2003 | Moody, III |
| 6,527,711 B1 | 3/2003 | Stivoric et al. |
| 6,541,679 B2 | 4/2003 | Betrabet et al. |
| 6,543,099 B1 | 4/2003 | Fillion et al. |
| 6,561,354 B1 | 5/2003 | Fereshtehkhou et al. |
| 6,562,167 B2 | 5/2003 | Coenen et al. |
| 6,564,436 B2 | 5/2003 | Black et al. |
| 6,606,771 B2 | 8/2003 | Curtis et al. |
| 6,608,118 B2 | 8/2003 | Kosaka et al. |
| 6,610,383 B1 | 8/2003 | Morman et al. |
| 6,613,032 B2 | 9/2003 | Ronnberg et al. |
| 6,613,113 B2 | 9/2003 | Minick et al. |
| 6,675,429 B2 | 1/2004 | Carter et al. |
| 6,720,362 B1 | 4/2004 | Park et al. |
| 6,725,512 B2 | 4/2004 | Carter |
| 6,730,069 B2 | 5/2004 | Tanzer et al. |
| 6,735,833 B2 | 5/2004 | Putnam et al. |
| 6,743,213 B1 | 6/2004 | Minato et al. |
| 7,112,257 B2 * | 9/2006 | Baggot et al. ............... 162/109 |
| 7,297,139 B2 * | 11/2007 | Price et al. ................. 604/391 |
| 2002/0025753 A1 | 2/2002 | Putnam et al. |
| 2002/0037390 A1 | 3/2002 | Shepard |
| 2002/0146957 A1 | 10/2002 | Fuller et al. |
| 2003/0077430 A1 | 4/2003 | Grimm et al. |
| 2003/0121128 A1 | 7/2003 | Vanbenschoten |
| 2003/0199844 A1 | 10/2003 | LaVon et al. |
| 2004/0024379 A1 | 2/2004 | LaVon et al. |
| 2004/0086320 A1 | 5/2004 | Policicchio et al. |

| | | | |
|---|---|---|---|
| 2004/0097856 A1 | 5/2004 | Cipra et al. | |
| 2004/0157036 A1 | 8/2004 | Provost et al. | |
| 2004/0161994 A1 | 8/2004 | Arora et al. | |
| 2004/0229067 A1 | 11/2004 | Baggot et al. | |
| 2005/0132518 A1 | 6/2005 | Chen et al. | |
| 2005/0132519 A1 | 6/2005 | Chen et al. | |
| 2005/0136238 A1 | 6/2005 | Chen et al. | |
| 2005/0136781 A1 | 6/2005 | Haynes et al. | |
| 2005/0148984 A1 | 7/2005 | Lindsay et al. | |

FOREIGN PATENT DOCUMENTS

| | | | |
|---|---|---|---|
| DE | 1297331 | 6/1969 | |
| EP | EP 0071671 B1 | 5/1985 | |
| EP | 0191475 A2 | 8/1986 | |
| EP | 0923902 A2 | 6/1999 | |
| EP | 1113518 A1 | 7/2001 | |
| GB | 1443024 | 7/1976 | |
| JP | 2001179684 A | 7/2001 | |
| WO | WO 9114731 A1 | 10/1991 | |
| WO | WO 9118574 A1 | 12/1991 | |
| WO | WO 9701310 A1 | 1/1997 | |
| WO | WO 9701312 A1 | 1/1997 | |
| WO | WO 9749361 A1 | 12/1997 | |
| WO | WO 9828118 A1 | 7/1998 | |
| WO | WO 9829063 A1 | 7/1998 | |
| WO | WO 9829064 A1 | 7/1998 | |
| WO | WO 9852458 A1 | 11/1998 | |
| WO | WO 9909917 A1 | 3/1999 | |
| WO | WO 9909918 A1 | 3/1999 | |
| WO | WO 9923160 A1 | 5/1999 | |
| WO | WO 9944254 A1 | 9/1999 | |
| WO | WO 0015697 A1 | 3/2000 | |
| WO | WO 0119302 A1 | 3/2001 | |
| WO | WO 0141622 A2 | 6/2001 | |
| WO | WO 0167911 A2 | 9/2001 | |
| WO | WO 0168019 A1 | 9/2001 | |
| WO | WO 0226872 A1 | 4/2002 | |
| WO | WO 03000104 A1 | 1/2003 | |

* cited by examiner

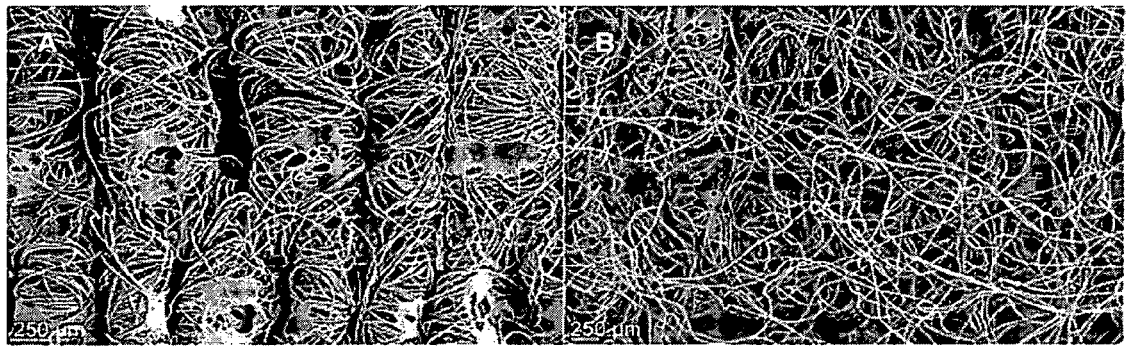
FIGURE 6A                    FIGURE 6B
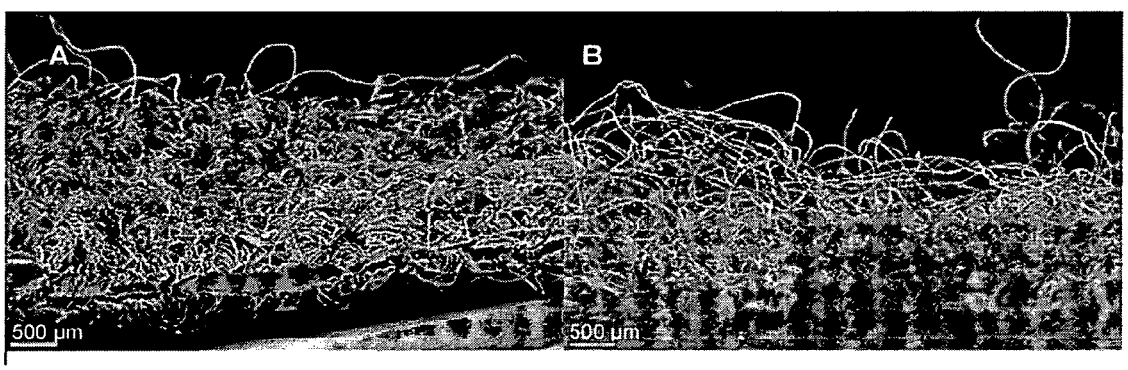
FIGURE 7A                    FIGURE 7B

METHODS TO MODIFY THE FIBROUS LANDING LAYER OF A FOAM BASED FASTENER AND PRODUCTS MADE FROM THE SAME

BACKGROUND OF THE INVENTION

Traditional hook and loop mechanical fasteners are widely used in numerous products and articles such as diapers, shoes, disposable gowns, etc. In spite of their prevalence, they suffer from several drawbacks. The hook material is typically stiff and impermeable. Also, when used in articles worn on or near the human body, the hook material may irritate the skin or be uncomfortable. The hook material typically cannot be stretched or deformed significantly. Further, for some applications, the entanglement of hooks into loop material can frequently be difficult to remove, or may adhere to unintended surfaces. The highly abrasive nature of the hook material can also damage some surfaces. The act of peeling the hooks and loops apart can also result in a loud and unpleasant noise, making it difficult to release a fastener discreetly. Further still, in some applications, low peel strength but high resistance to shear is desired, whereas conventional hook and loop fasteners may offer excessively high peel strength to achieve a given level of shear resistance.

Variations of hook and loop fasteners have been proposed in which a foam layer is used to engage with hooks, but replacing low cost, flexible loop material with thicker, generally more expensive foams does not appear to have provided significant advantages, and does not address the known limitations of hook layers. Hook and loop fasteners have also been proposed in which an added foam section provides increased friction for a fastening member in a securing zone, but such proposals does not overcome the inherent limitations of hook materials.

Foam based fasteners are disclosed in U.S. patent application Ser. No. 10/956,613, filed on Sep. 30, 2004, and naming as inventors F. J. Chen et. al. which is incorporated by reference herein in its entirety. The Ser. No. 10/956,613 application describes an improved mechanical fastener that solves one or more of the aforementioned problems. Further improvements, however, are still needed.

According to the present disclosure, methods for improving the landing layers of the improved mechanical fastener are generally described. Resulting from these methods, the landing layers can exhibit improved attachment to the foam layer of the mechanical fastener. For example, the methods of the present disclosure can result in a mechanical fastener with an increased resistance of shear movement of the engaged layers. Furthermore, by subjecting materials to the methods of this invention, a wider and improved selection of materials for the landing layer can be provided.

SUMMARY OF THE INVENTION

The present disclosure is generally directed to methods for improving the engagement surface of the landing layer of a mechanical fastener. For example, in one embodiment, the present disclosure is generally directed to a method of increasing the shear resistance of a mechanical fastener comprising a foam layer and a landing layer. The landing layer comprises a fibrous web having an engaging surface. The mechanical fastener has a shear resistance between the foam layer and the landing layer. According to this embodiment, the engaging surface of the landing layer is mechanically modified to increase the shear resistance between the foam layer and the landing layer. For example, the shear resistance between the foam layer and the landing layer can be at least about 25% greater than the shear resistance of the mechanical fastener prior to modification of the engaging surface of the landing layer. For instance, in one embodiment the shear resistance can be at least about 50% greater than the shear resistance prior to modification, such as greater than about 75%. For instance, in one embodiment, the shear resistance of the mechanical fastener after modification of the engaging surface of the landing layer can be at least about twice as much as the shear resistance prior to modification.

The landing layer can comprise a nonwoven fibrous web, such as a spunbond web or a bonded carded web. The foam layer can comprise an open celled foam, such as a melamine foam or a polyurethane foam.

In another embodiment, a method of increasing the perimeter/edge-length ratio of a landing layer of a mechanical fastener is generally provided. For example, the method can comprise providing a mechanical fastener having a foam layer and a landing layer. The landing layer can comprise a fibrous web defining an engaging surface. The engaging surface of the landing layer can be mechanically modified to increase the perimeter/edge-length ratio by at least about 50%, such as at least about 75%. For instance, in one embodiment, the engaging surface of the landing layer can be mechanically modified to increase the perimeter/edge-length ratio by at least about 100% (i.e. at least about twice as much).

Exemplary methods of modifying the engaging surface of the landing layer can be brushing, necking in the cross machine direction, stretching in the machine direction, needle punching, hydroentangling, dragging over an edge, or dragging over an ultrasonic horn.

In another embodiment, the present disclosure is generally directed to a mechanical fastener having improved shear resistance. The mechanical fastener comprises a landing layer and a foam layer. The landing layer defines a first engaging surface that has been mechanically modified to increase the perimeter/edge-length ratio by at least about 50%. The landing layer can comprise a nonwoven fibrous web. The foam layer defines a second engaging surface. The first engaging surface of the landing layer can mechanically attach to the second engaging surface of the foam layer.

Various features and aspects of the present invention will be made apparent from the following detailed description.

DEFINITIONS

As used herein, the term "reticulated foam", as it is commonly used among those skilled in the art, denotes solid foamed materials where substantially all intervening "window walls" or cell membranes have been removed from the cells of the foam, leaving a network consisting primarily of interconnected struts along the outlines of the cells formed during the foaming.

Reticulated foams are thus distinct from foams in which the window walls are merely broken, or foams in which only the outermost window walls or skin have been removed by physical means. Reticulated foams, by virtue of their general lack of cell membranes, are highly permeable to gas and liquid alike, offering little resistance to fluid flow, indeed much less than those foams in which the cell membranes have been retained.

Reticulation is typically achieved by known foam processing procedures applied to the foam after the cells have been formed. These procedures may involve the use of caustic treatments (e.g., see U.S. Pat. No. 3,266,927, issued to Lorenz, et al. on Aug. 16, 1966), attack by other reactive compounds such as ozone, or thermal treatments of the foam, removing all or substantially all of the "window walls" separating the cells throughout the foam. In some cases, other treatments such as controlled explosions are used to remove membranes around portions of cells (for example, a foam may be packed into an explosion chamber containing an explosive gaseous medium which is then exploded). An example of explosive treatment of a foam is given in U.S. Pat. No. 4,906,263, issued to von Blucher et al. on Mar. 6, 1990.

Needling may also be used to open a closed cell foam material, as described in U.S. Pat. No. 4,183,984, issued to Browers et al. on Jan. 15, 1980. Other methods for creating an open cell foam material are disclosed in U.S. Pat. No. 6,720, 362, issued to Park et al. on Apr. 13, 2004.

In one embodiment of the present invention, reticulation is only present in the outer portions of a foam layer at and near the engaging surface.

Alternatively, the cellular foam material may be inherently reticular as made. According to U.S. Pat. No. 3,661,674, issued to Higgs et al. on May 9, 1972, an inherently reticular polyester polyurethane foam may be made, for example, by allowing the foam-forming ingredients to react in the presence of a viscosity-retarding substance such as a further polyester having an acid component which is the same as that of the polyester used to make the foam material but which has a hydroxyl number of between 10 and 100 and a viscosity of less than 200 poises.

As used herein, the phrase "cluster of free-standing struts" refers to one or more interconnected struts that extend away from a complete cell of the foam material, wherein the struts in the cluster are connected to the same complete cell. If first and second struts from first and second cells, respectively, join at a juncture and have a third strut (a free-standing strut) extending from the juncture, the first and second struts are considered to be part of a closed cell, and the cluster of free-standing struts would consist of the third strut. If the third strut branches into two other free-standing struts at an end away form the juncture, the third strut and the two other free-standing struts are all part of a cluster of free-standing struts.

As used herein, the term "free length" of a free-standing strut or cluster of free-standing struts is the linear distance the free-standing strut or cluster of free-standing struts, respectively, extends away from the nearest portion of the first complete cell in the foam material attached to the free-standing strut or cluster of free-standing struts.

As used herein, the term "nonwoven fabric or web" means a web having a structure of individual fibers or threads which are interlaid, but not in an identifiable manner as in a knitted fabric. Nonwoven fabrics or webs have been formed from various processes such as, for example, meltblowing processes, spunbonding processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91).

As used herein, the term "composite" refers to a material which may be a multicomponent material or a multilayer material. These materials may include, for example, spunbond-meltblown-spunbond, stretch bonded laminates, neck bonded laminates, or any combination thereof.

As used herein, the term "spunbonded fibers" refers to small diameter fibers which are formed by extruding molten thermoplastic material as filaments from a plurality of fine, usually circular capillaries of a spinneret with the diameter of the extruded filaments then being rapidly reduced to fibers as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al., the entire contents of which are incorporated herein by reference in their entirety for all purposes. Spunbond fibers are generally continuous and have diameters generally greater than about 7 microns, more particularly, between about 10 and about 40 microns.

As used herein, the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al., the entire contents of which are incorporated herein by reference in their entirety for all purposes. Meltblown fibers are microfibers which may be continuous or discontinuous with diameters generally less than 10 microns.

As used herein, the term "stretch bonded laminate" refers to a composite material having at least two layers in which one layer is a gatherable layer and the other layer is an elastic layer. The layers are joined together when the elastic layer is extended from its original condition so that upon relaxing the layers, the gatherable layer is gathered. Such a multilayer composite elastic material may be stretched to the extent that the nonelastic material gathered between the bond locations allows the elastic material to elongate. One type of stretch bonded laminate is disclosed, for example, by U.S. Pat. No. 4,720,415 to Vander Wielen et al., the entire contents of which are incorporated herein by reference in their entirety for all purposes. Other composite elastic materials are disclosed in U.S. Pat. No. 4,789,699 to Kieffer et al., U.S. Pat. No. 4,781, 966 to Taylor and U.S. Pat. Nos. 4,657,802 and 4,652,487 to Morman and U.S. Pat. No. 4,655,760 to Morman et al., the entire contents of which are incorporated herein by reference in their entirety for all purposes.

As used herein, the term "coform" means a meltblown material to which at least one other material is added during the meltblown material formation. The meltblown material may be made of various polymers, including elastomeric polymers. Various additional materials may be added to the meltblown fibers during formation, including, for example, pulp, superabsorbent particles, cellulose or staple fibers. Coform processes are illustrated in commonly assigned U.S. Pat. No. 4,818,464 to Lau and U.S. Pat. No. 4,100,324 to Anderson et al., the entire contents of which are incorporated herein by reference in their entirety for all purposes.

As used herein, the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

BRIEF DESCRIPTION OF THE FIGURES

A full and enabling disclosure of the present invention, including the best mode thereof, directed to one of ordinary skill in the art, is set forth in the specification which includes and makes reference to the appended figures in which:

FIG. 6A is an overhead SEM picture of an exemplary engagement surface of a landing layer before treatment;

FIG. 6B is an overhead SEM picture of the exemplary engagement surface of the landing layer of FIG. 6A after treatment;

FIG. 7A is a side view SEM picture of the exemplary engagement surface of the landing layer of FIG. 6A before treatment;

FIG. 7B is a side view SEM picture of an exemplary engagement surface of the landing layer of FIG. 7A after treatment;

Figure 1:
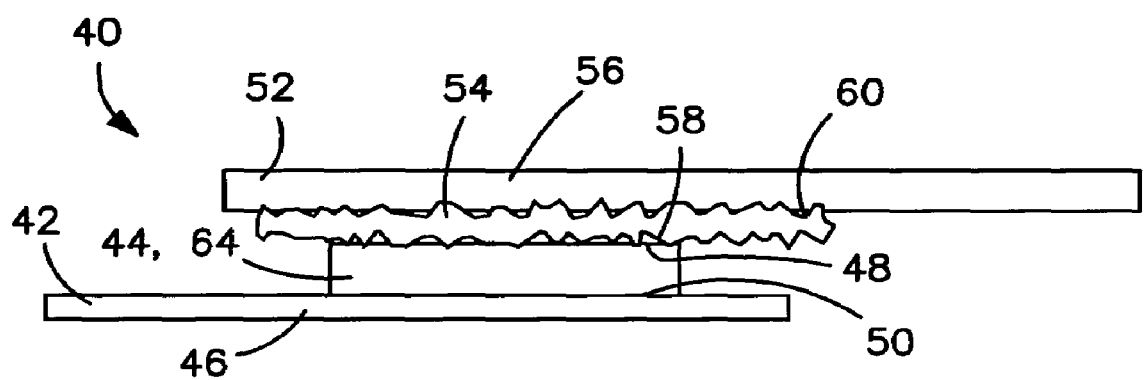
FIG. 1 depicts an exemplary embodiment of a cross-sectional view of a foam layer fastening system according to the present invention.

Repeat use of reference characters throughout the present specification and appended drawings is intended to represent the same or analogous features or elements of the invention.

Unless otherwise stated, the Scanning Electron Microscope ("SEM") pictures were taken with a SEM sold under the trade name JEOL 840 SEM by JEOL-USA, located in Peabody, Mass.

DETAILED DESCRIPTION OF THE INVENTION

Reference now will be to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary instructions.

FIG. 1 depicts an exemplary embodiment of a fastening system 40 according to the present disclosure. The fastening system 40 has a first engaging portion 42 comprising a foam layer 44 joined to a first member 46. The first engaging portion 42 is shown attached to a second engaging portion 52 comprising a landing layer 54 joined to a second member 56. The foam layer 44 has an engaging surface 48 and a remote surface 50 joined to the first member 46. Likewise, the landing layer 54 has an engaging surface 58 and a remote surface 60. The foam layer 44 is depicted as a simple layer of foam material 64 alone, but could also comprise an integral reinforcing layer (not shown) on the remote surface 50 of the foam material 64.

The first and second members 46 and 56, respectively, could be any two surfaces that are desirable to be joined by mechanical fasteners and could comprise, for example, fabrics, films, composite articles, wood, glass, metal, medical devices, automotive components, non-woven webs, paper, tissue, and the like.

Figure 2:
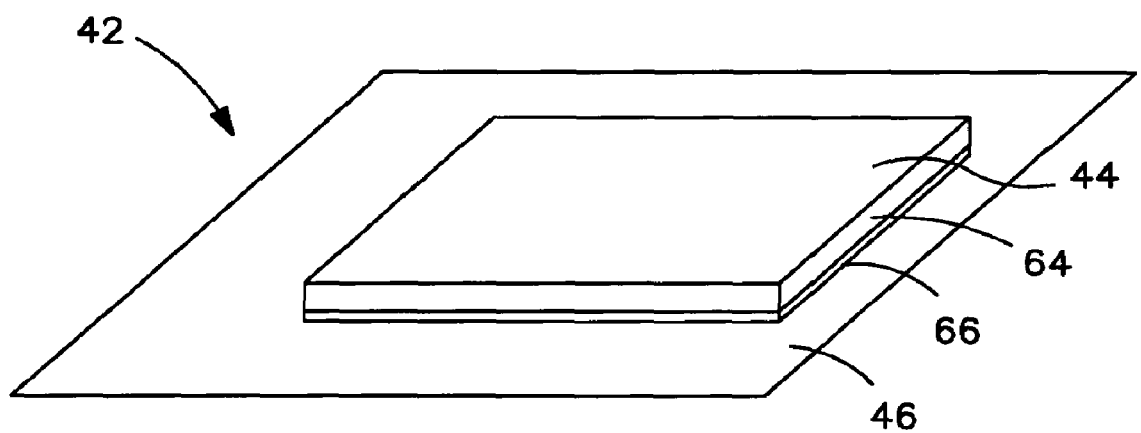
FIG. 2 depicts an exemplary embodiment of a perspective view of a foam layer fastening system according to the present invention.

FIG. 2 depicts another embodiment of the first engaging portion 42 of a foam layer fastening system 40 in which the foam material 64 of the foam layer 44 is joined to a reinforcing layer 66.

Figure 3:
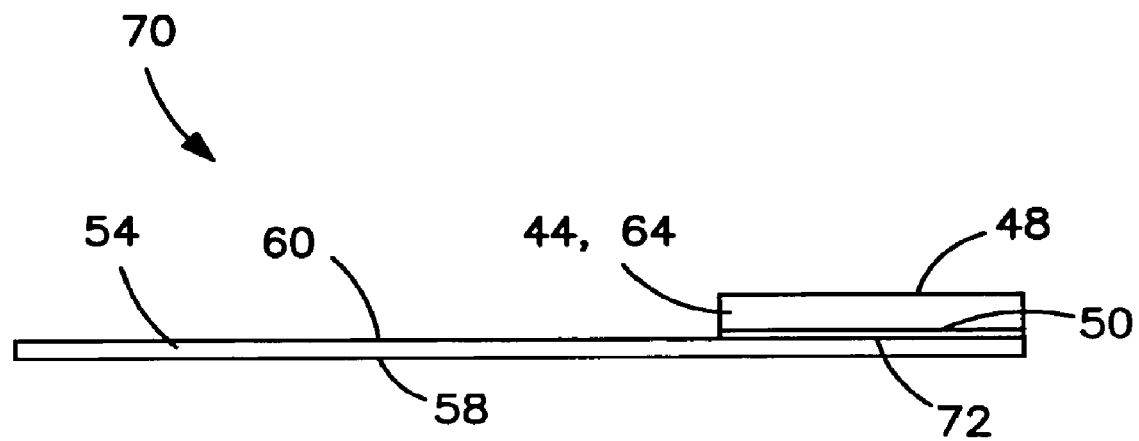
FIG. 3 depicts another exemplary embodiment of a self-adhesive strip of the present invention comprising a foam layer joined to a length of landing layer.

FIG. 3 depicts yet another embodiment of the present disclosure, wherein the mechanical system is used on a self-adhesive strip 70. The self-adhesive strip 70 comprises a foam layer 44 joined to a length of landing layer 54 by attachment means 72, which comprise adhesive, ultrasonic bonds, a thermal weld involving fused thermoplastic material, and so forth. The engaging surface 58 of the landing layer 54 is depicted as remote from the engaging surface 48 of the foam layer 44 (i.e., the two engaging surfaces 48 and 58 are on opposite sides of the self-adhesive strip 70). However, in other embodiments, the engaging surface 58 of the landing layer 54 may also be on the same side of the self-adhesive strip 70 as the foam layer 44, or both surfaces of the landing layer 54 may be adapted to engage with foam material 64 of the foam layer 44.

The mechanical fasteners of the present disclosure can be utilized in any application where a mechanical fastener may be desirable. For example, the mechanical fasteners can be utilized on disposable absorbent articles, such as diapers, training pants, adult incontinence products, and the like. It is to be understood by one of ordinary skill in the art that the present disclosure is not limited by the end use of the mechanical fastening device disclosed.

The mechanical fastening devices described in the present disclosure comprise a foam layer and a landing layer. For example, in one embodiment, the foam layer can comprise an open-celled foam, such as a melamine foam, a polyurethane foam, or other open-celled foams. As used herein, a foam material is "open-celled" if at least 60% of the cells in the foam structure that are at least one micrometer in size are in fluid communication with at least one adjacent cell. In one embodiment, at least 80% of the cells in the foam structure that are at least one micrometer in size are in fluid communication with at least one adjacent cell.

Such foam materials typically comprise rod-like struts forming a reticulated network that defines cells in the foam materials. The free standing struts of the foam material, by way of example only, may have an affective diameter of about 0.03 microns or greater, such as about 1 micron or greater, about 3 microns or greater, or about 10 microns or greater. For example, the struts can have an affective diameter of from about 0.3 microns to about 30 microns, from about 1 micron to about 30 microns, from about 3 microns to about 30 microns, from about 1 micron to about 20 microns, and from about 1 micron to about 10 microns.

Suitable foam materials include, but are not limited to, melamine foam, polyurethane foam, polyester and polyether types, as well as other known reticulated foams. The foam layer may also comprise more than one kind of foam. In some embodiments, the foam layer may be reinforced with an underlying reinforcing layer, such as a non-woven web, a tissue web, a woven fabric, a scrim material, and the like. When used, the reinforcing web can be attached to the foam material by any means suitable for maintaining good flexibility in the article.

Figure 4:
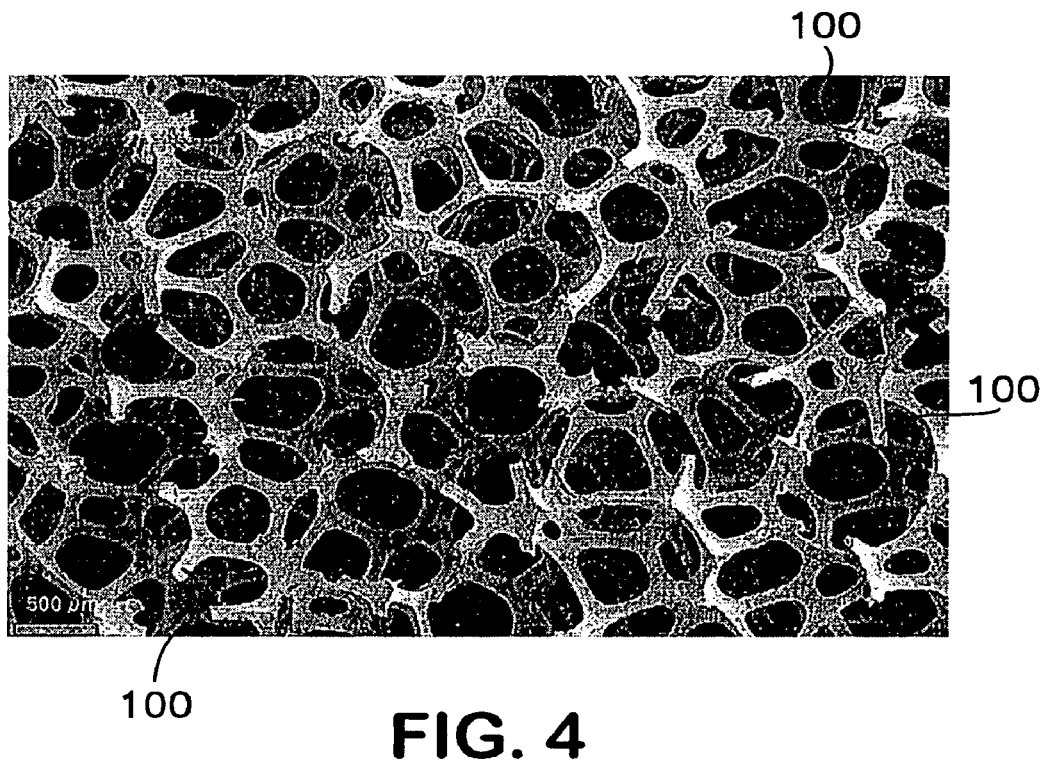
FIG. 4 is a SEM picture of an exemplary embodiment of an engaging surface of a foam layer.

Referring to the exemplary embodiment of FIG. 4, a SEM picture at 20× magnification of an exemplary engaging surface of a foam layer is shown. The pictured foam layer is a polyurethane foam sold under the trade name FOAMEX® Z60B by Foamex, Inc., located in Linwood, Pa.

Figure 5:
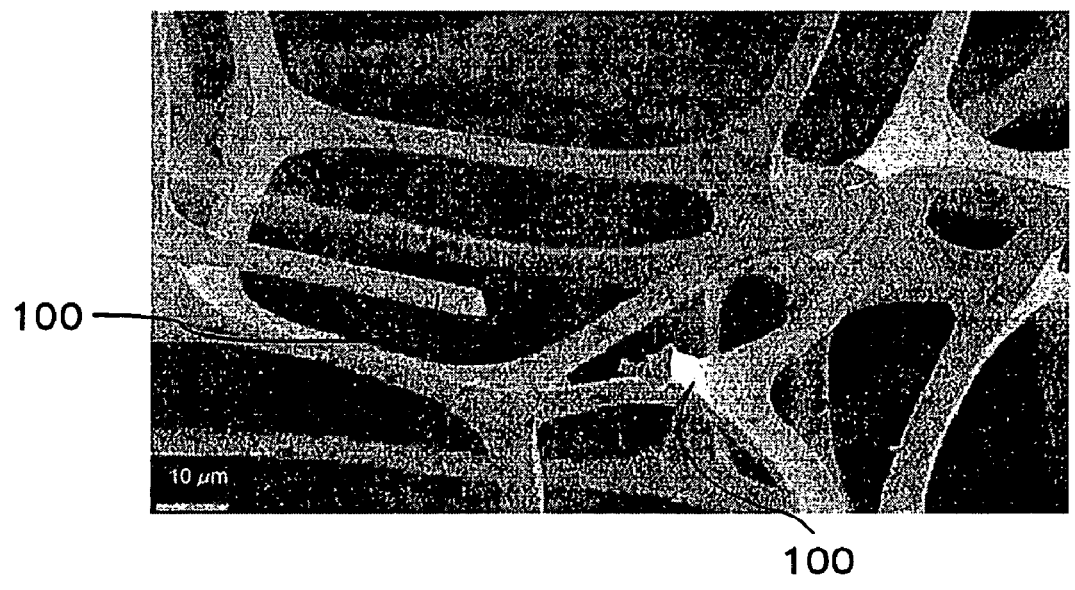
FIG. 5 is SEM picture of another exemplary embodiment of an engaging surface of a foam layer.

FIG. 5 is a SEM picture at 750× magnification of another exemplary engaging surface of a foam layer. The pictured foam layer is a melamine foam designated BASOTECH® foam sold by BASF Corporation, located in Ludwigshafen, Germany.

Both of the exemplary foam layers shown in FIGS. 4 and 5 have engaging surfaces with free-standing struts 100 available to engage an engaging surface of a landing layer.

The landing material for use in the landing layer of the present disclosure may be a loop material from existing hook and loop fastening systems. For best results, the size of the loops or holes in the landing layer can be designed for the most effective attachment with the foam layer being used.

The landing material may be a fibrous web providing hook-engagable, free-standing loops extending from at least one surface of the material. Landing layers can be made from woven textiles or non-woven fabrics. The landing material may be a non-woven web, such as, but not limited to, a meltblown web, a spunbond web, a bonded carded web, a spunlace web, a coform web, and combinations thereof.

Also, the web may be a needle punched or hydroentangled web. For instance, in one embodiment, the landing layer can comprise a spunbond web that has been hydroentangled with pulp fibers, such as the web sold under the trade name HYDROKNIT® by Kimberly Clark Corporation, Inc. of Neenah, Wis. and discussed in greater detail in U.S. Pat. No. 5,284,703, which is incorporated herein by reference in its entirety.

The landing material can also be a laminate of two or more webs. Loop materials that may be adapted for use as a landing layer include laminates of non-woven materials, such as non-woven webs joined to films or multiple layers of fibrous non-woven webs.

The landing layer may have an engaging surface with fibrous loops that lie in the plane of the fabric giving a flat appearance. Or the loops may rise above the plane of the fabric giving a fuzzy or lofty appearance. For example, the size of the fibers of the landing layer can be selected according to the size of the respective struts of the foam layer. For instance, optimization of the fitting between the struts of the foam layer and the fibers of the landing layer can be realized by comparing the size of the struts to the size of the fibers. The present inventors have discovered that, in one embodiment, meltblown webs can have improved shear resistance when used as landing layers with foam layers having fine struts. Also, in an alternative embodiment, when coarse foam layers are used, spunbond webs can be used as the landing layer for improved shear resistance.

Landing layers may comprise a single type of fibers or a plurality of fiber types or compositions. For instance, the fibers may be made from numerous polymers such as cellulose, polyolefins, polyamides, polyesters, polylactic acid, acrylic, and the like. Landing layers may also include electrospun fibers, which are commonly referred to as nanofibers. The landing layers can also comprise bicomponent fibers.

Also, loop materials may be adapted for use in a landing layer of the present disclosure. Loop materials that may be adapted for use in the landing layer can include laminates of non-woven materials, such as non-woven webs joined to films or multiple layers of fibrous non-woven webs.

In some embodiments, the landing layer may comprise openings in its engaging surface, which may be engaged by free-standing struts in a foam layer. For example, the openings may be pores in the surface of the landing layer defined by the surrounding fibers.

In other embodiments, the landing layer can comprise fine microfibers that may provide loop elements to engage the free-standing struts of the foam layer. Alternatively, the microfibers can be provided in a spun-lace web in which microfibers have been hydroentangled on a non-woven or woven backing layer.

According to the present disclosure, the engaging surface of the landing layer is subjected to a process to improve engagement of the landing layer with the foam layer by increasing the availability for engagement of the fibers and fibrous loops in the landing layer. For example, the present inventors have discovered that the ability of fibrous materials to attach to the foam material can be improved through a single or a combination of changes in the properties of the landing layer. For instance, increasing the loftiness of the engaging surface favors the strength of the engagement in most cases. Also, increasing the available fiber length of the fiber between bond points of the fibrous layer can improve engagement. In addition, when the fibers of the landing layer are smaller than the struts of the foam, improved engagement can be realized.

Also, in one embodiment, the present inventors have discovered that fibrous webs having sufficient openings or pores can engage struts of the foam layer to produce a better engagement. For example, greater than about 50% of the engaging surface of the fibrous web can comprise open space, such as greater than about 60%. Accordingly, very dense and flat webs can actually hinder the engagement of the fibrous web to the foam layer. Likewise, embossed surface structures can hinder the engagement of the fibrous web to the foam layer because the struts may ride on top of the web and cannot reach the fibers in the troughs. On the other hand, landing layers with increased fuzziness can improve attachment of the landing layer to the foam layer.

Accordingly, the treatment processes of the present disclosure can mechanically modify the fibrous surface of the landing layer to increase attachment with the foam layer. Any method of treatment can be utilized to modify the fibrous surface of the landing layer.

In some embodiments, modification of the fibrous surface of the landing layer can result in a mechanical fastener comprising a landing layer and a foam layer with improved shear resistance. For example, in one embodiment, modification of the fibrous surface can result in a mechanical fastener having at least about 25% greater shear resistance than the same fastener prior to modification of the fibrous surface, such as greater than about 50%. For instance, in some embodiments, modification of the fibrous surface can result in a mechanical fastener having at least about 75% greater shear resistance than the same fastener prior to modification of the fibrous surface, such as greater than about 90%. In one particular embodiment, the modified fibrous surface can result in a mechanical fastener having at least about 100% (i.e. twice as much) of the shear resistance of the same fastener prior to modification.

Also, in some embodiments, the surface fuzziness on the engaging surface of landing layer, such as a fibrous material, can be increased by mechanical treatment. The surface fuzziness on the engaging surface of the landing layer can be quantified through a measurement of the fuzz on edge of the surface.

One measurement that infers the fuzz on edge of a surface is the perimeter/edge-length ratio (PR/EL), as discussed in detail in US Patent Publication No. 2004/0229067 of Baggot, et al., filed on Jan. 7, 2004, which is incorporated by reference in its entirety. The PR/EL value is the sum of the perimeters of the counted fibers divided by the length of edge over which they were counted.

According to the methods of the present disclosure, modification of the surface of the landing layer can result in a modified landing layer having at least about a 25% increase in its PR/EL, such at greater than about 50% increase. For instance, in some embodiments, the PR/EL of the landing layer can be increased by greater than about 75%, such as greater than about 100% (i.e. at least twice as much). In one particular embodiment, the PR/EL of the landing layer can be increased by greater than about 150%, such as greater than about 200%.

Another measurement that infers the fuzz on edge of a surface is the number of fiber fragments per field of view of the surface. For instance, as the number of fiber fragments per field of view increases, the fuzz on edge of the surface increases.

In one embodiment, the fibrous surface of the landing layer can be brushed. Brushing the fibrous surface of the landing layer can be accomplished by a number of mechanisms. For example, the fibrous surface can be carded, dragged across a rough or patterned surface or roll, or picked with a roughened surface having barbs, hooks or the like. Also, the fibrous surface can be dragged through a nip, such as a rubber surface on steel rolls run at different speeds. If the fibrous landing layer is a part of a laminate, the brushing can be done to the base fibrous web or the laminate.

In one embodiment, the engaging surface of the landing layer can be mechanically napped by the use of a napping machine, such as the napping machine sold under the trade name VELURA by Saspe S.r.l. of Schio (VI) Italy. Napping machines are well known to one of ordinary skill in the art, and have been disclosed as early as 1891 in U.S. Pat. No. 458,725, which is hereby incorporated by reference. For instance, napping the engaging surface of the landing layer can pluck some fibers away from the surface producing a higher fuzziness.

In other embodiments, the landing layer can be drawn or necked in the machine direction. For example, "necking" or "neck stretching" can elongate a nonwoven fabric, generally in the machine direction, to reduce its width (cross-machine direction) in a controlled manner to a desired amount. The controlled stretching may take place under cool, room temperature or greater temperatures and is limited to an increase in overall dimension in the direction being stretched up to the elongation required to break the fabric, which in most cases is about 1.2 to 1.6 times. When relaxed, the web retracts toward, but does not return to, its original dimensions. Such a process is disclosed, for example, in U.S. Pat. No. 4,443,513 to Meitner and Notheis, U.S. Pat. Nos. 4,965,122, 4,981,747 and 5,114,781 to Morman and U.S. Pat. No. 5,244,482 to Hassenboehler Jr. et al., the entire contents of which are incorporated herein by reference in their entirety for all purposes. As used herein, the term "reversibly necked material" refers to a material that possesses stretch and recovery characteristics formed by necking a material, then heating the necked material, and cooling the material. Such a process is disclosed in U.S. Pat. No. 4,965,122 to Morman, the entire contents of which are incorporated by reference herein in their entirety for all purposes.

As used herein, the term "neck bonded laminate" refers to a composite material having at least two layers in which one layer is a necked, non-elastic layer and the other layer is an elastic layer. The layers are joined together when the non-elastic layer is in an extended (necked) condition. Examples of neck-bonded laminates are such as those described in U.S. Pat. Nos. 5,226,992, 4,981,747, 4,965,122 and 5,336,545 to Morman, the entire contents of which are incorporated herein by reference in their entirety for all purposes.

In yet other embodiments, the landing layer can be stretched in the cross-direction, such as by using grooving rolls or a tentor frame. As used herein, the terms "stretch" or "stretched" refers to the ability of a material to extend upon application of a biasing force. Percent stretch is the difference between the initial dimension of a material and that same dimension after the material has been stretched or extended following the application of a biasing force. Percent stretch may be expressed as [(stretched length B initial sample length)/initial sample length]×100. For example, if a material having an initial length of one (1) inch is stretched 0.50 inch, that is, to an extended length of 1.50 inches, the material can be said to have a stretch of 50 percent.

In some instances, the stretched material can recover. "Recovery" refers to a contraction of a stretched material upon termination of a biasing force following stretching of the material by application of the biasing force. For example, if a material having a relaxed, unbiased length of one (1) inch is elongated 50 percent by stretching to a length of one and one half (1.5) inches the material would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its elongation.

Also, in other embodiments, the fibrous surface of the landing layer can be subjected to high-velocity air or water jets. For example, the fibrous surface of the landing layer can be hydroentangled. Generally, hydroentangling a web involves impacting the fibrous web with a working fluid, typically water, at relatively high pressures. For example, hydroentangling is disclosed in U.S. Pat. No. 3,485,706 issued to Evans and U.S. Pat. No. 5,284,703 issued to Everhart, et al., both of which are incorporated herein by reference.

The fibrous surface of the landing layer can be dragged over an edge or an ultrasonic horn, in another embodiment. In still further embodiments, the fibrous surface of the landing layer can be needle punched.

The use of high-loft, high-crimp fibers, as with side-by-side bi-component spunbond fibers, can, in some embodiments, increase the landing layer's surface properties to increase its attachment to the foam layer. The use of high-loft, high-crimp fibers increases the number of fibers per area while maintaining sufficient space between the fibers for the struts to penetrate into the surface of the landing layer.

Other methods can be utilized to help the landing layer retain its loft through further processing or converting into product and packaging, which can increase the landing layer's attachment properties, and in particular, can increase the shear between the landing layer and the foam layer.

Reference now will be made to various embodiments of the invention, one or more examples which are set forth below. Each example is provided by way of explanation of the invention, not as a limitation of the invention. In fact, it will be apparent to those skilled in the art that various modifications and variations may be made of this invention without departing from the scope or spirit of the invention.

EXAMPLE 1

Each of the following fibrous materials were subjected to a mechanical modification process that increased the availability for engagement of the fibers in the engaging surface with reticulated foams. The engaging surface of each of the fibrous webs was mechanically modified with a 15 lb. hand roller that had a sheet of Velcro® 85-1065 (commercially available from Velcro USA Inc. of Manchester, N.H.) hook material wrapped around the outer surface, such that the hooks of the hook material extended away from the roll. The engaging surface of each fibrous non-woven web was treated with this hook wrapped roller by rolling the wrapped roller over the engaging surface two times back and forth in one direction and two times back and forth in a direction 90° to the first direction.

To assess how the mechanical treatment affected the ability of the fibrous non-woven webs to attach to reticulated foam, the shear strength of the mechanical fastener formed from the treated fibrous non-woven web (as the landing layer) and FOAMEX® Z60B (as the foam layer) was measured prior to treatment and after treatment. The shear strength was measured using a curved shear test method to measure the strength of attachment of the foam layer to the landing layer. The shear strength test method used is described in detail in the U.S. patent application Ser. No. 10/956,613.

Each of the following materials was tested, both prior to and after treatment, using the above test method:
1. A necked SMS, which was a spunbond/meltblown/spunbond (all layers comprising fiber grade polypropylene) laminate having been 52% necked and having a basis weight of 1.0 ounce/sq.yard.
2. A SBL, which was a stretch bond laminate (of spunbond polypropylene/elastic meltblown styrenic-block copolymer (Krayton G2760 sold by Krayton Polymers of Houston, Tex.)/spunbond polypropylene) having a basis weight of 2.098 ounce/sq.yard.
3. A necked spunbond, which was a 45% necked spunbond (polypropylene) having a basis weight of 0.4 ounce/sq.yard.

For example, FIGS. 6A and 7A depict the SBL prior to treatment according to this example, and FIGS. 6B and 7B depict the SBL after the treatment.

Figures 8A, 8B:
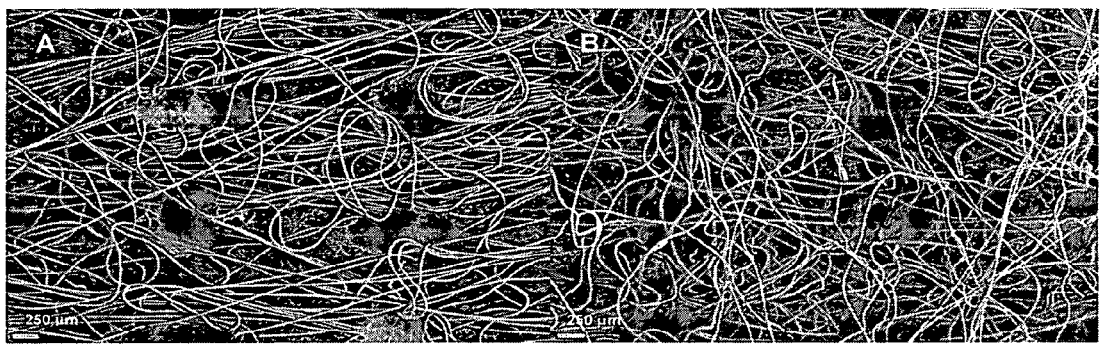
FIG. 8A is an overhead SEM picture of another exemplary engagement surface of a landing layer before treatment.
FIG. 8B is an overhead SEM picture of the exemplary engagement surface of the landing layer of FIG. 8A after treatment.
Figures 9A, 9B:
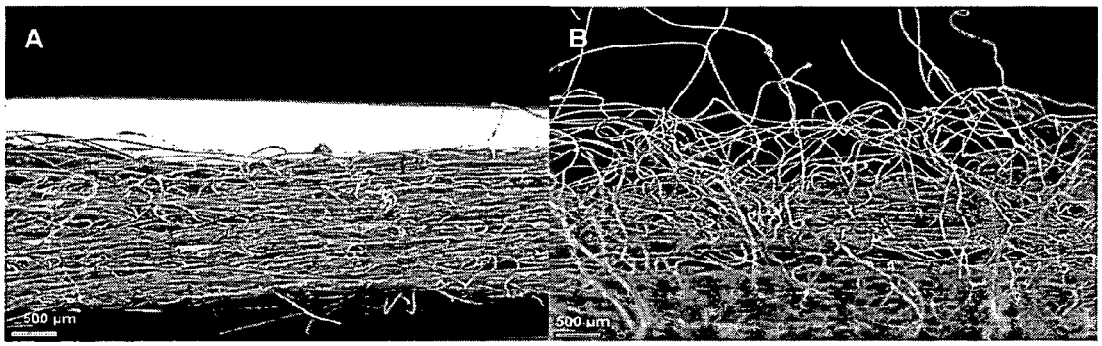
FIG. 9A is a side view SEM picture of the exemplary engagement surface of the landing layer of FIG. 8A before treatment.
FIG. 9B is a side view SEM picture of an exemplary engagement surface of the landing layer of FIG. 9A after treatment.

FIGS. 8A and 9A depict the necked SMS material prior to treatment according to this example, and FIGS. 8B and 9B depict the necked SMS after the treatment.

A measure of the strength of attachment of foam layers to landing layers of the present invention was obtained using a universal testing machine, an MTS Alliance RT/1 testing machine (commercially available from the MTS Systems Corp., located at Eden Prairie, Minn.) running with TestWorks® 4 software, version 4.04c, with a 100 N load cell.

Figure 10:
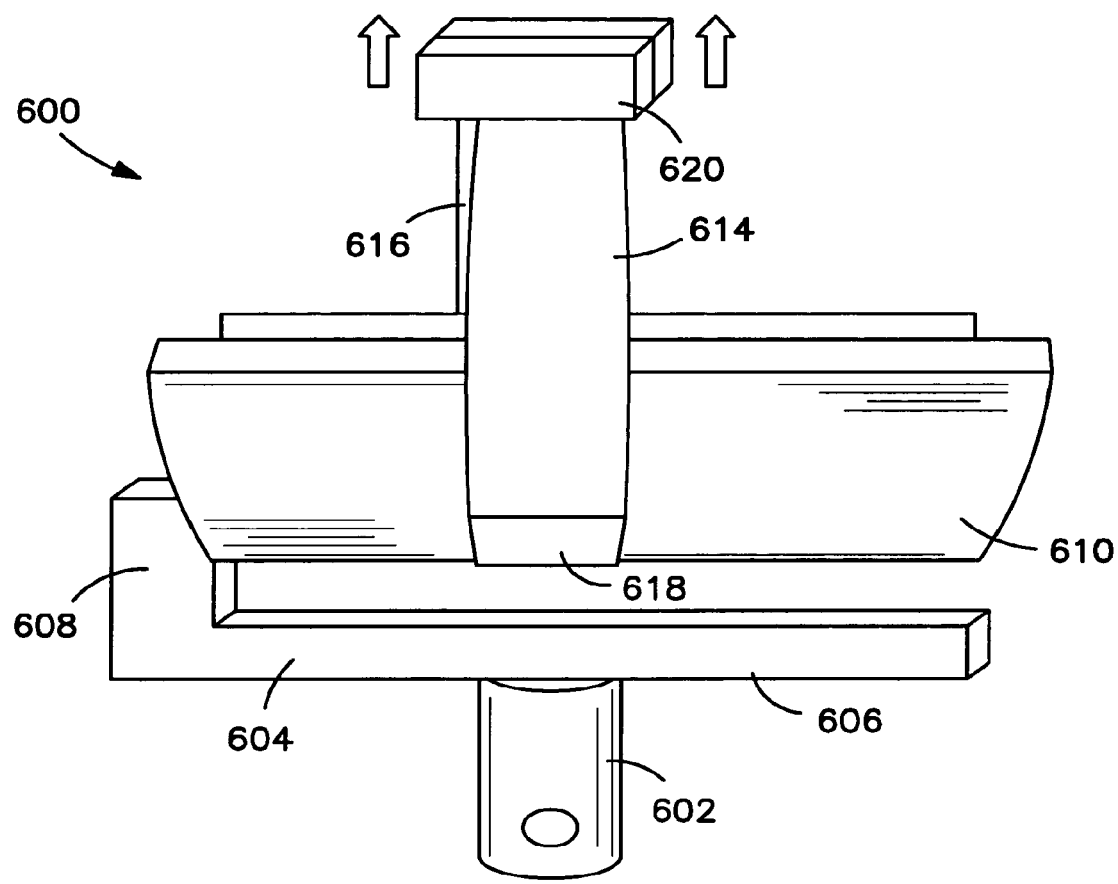
FIG. 10 depicts apparatus used for the Curved Shear Attachment Strength test.

For the test procedure, an upper clamp was used with rubber-lined jaws that are pneumatically loaded for good grasping of test samples. Into the lower mount of the test device was placed a special rig as shown in FIG. 10 which provided a curved surface against which an overlapping region of a foam layer and landing layer could be subject to tensile force. In FIG. 10, the test rig 600 comprises a cylindrical base 602 adapted for mounting into the lower mount of the universal testing machine (not shown), joined to an attachment section 604 comprising a horizontal beam 606 and a vertical beam 608 which is bolted into a curved section 610.

Figure 11:
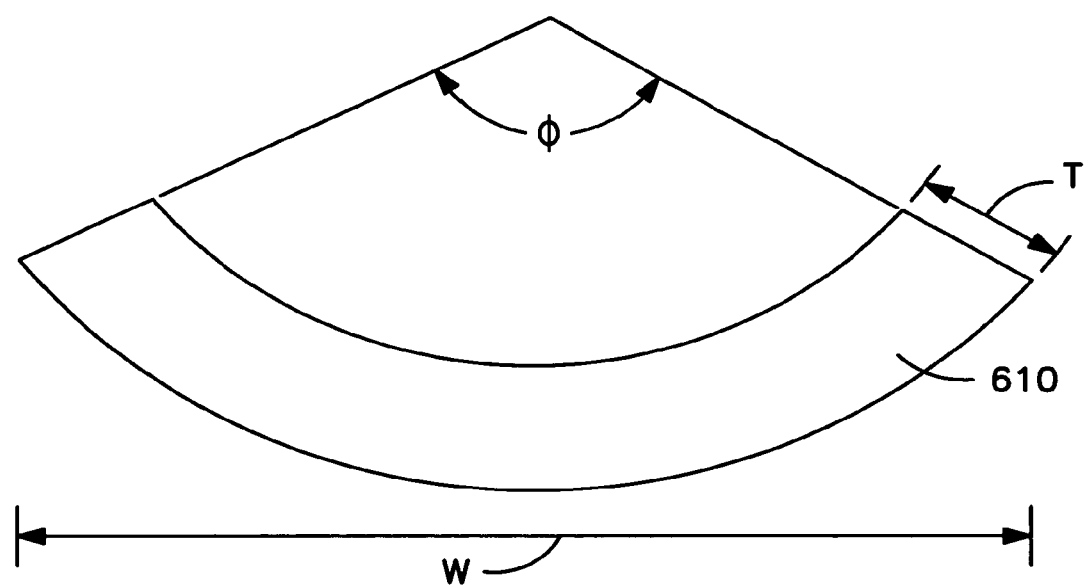
FIG. 11 shows the geometry of a side view of a curved section of the apparatus of FIG. 10.

Further details about the geometry of the curved section 610 are shown in the cross-sectional view of FIG. 11, which shows that the curved section 610 represents a circular arc subtending an angle φ of 110 degrees, has a thickness T of 0.5 inches, and a width W of 4.5 inches. The length of the curved section 610, the distance it extends into the plane of the paper in FIG. 11 (the left-to-right distance spanned by the curved section 610 in FIG. 10) is 8 inches. The curved section 610 made of rigid nylitron and has a smooth surface finish (a shape turned finish) of 32 microinches in roughness (a "32 finish") as measured with a Microfinish Comparator (Gar Electroforming, Danbury, Conn.).

Figure 12:
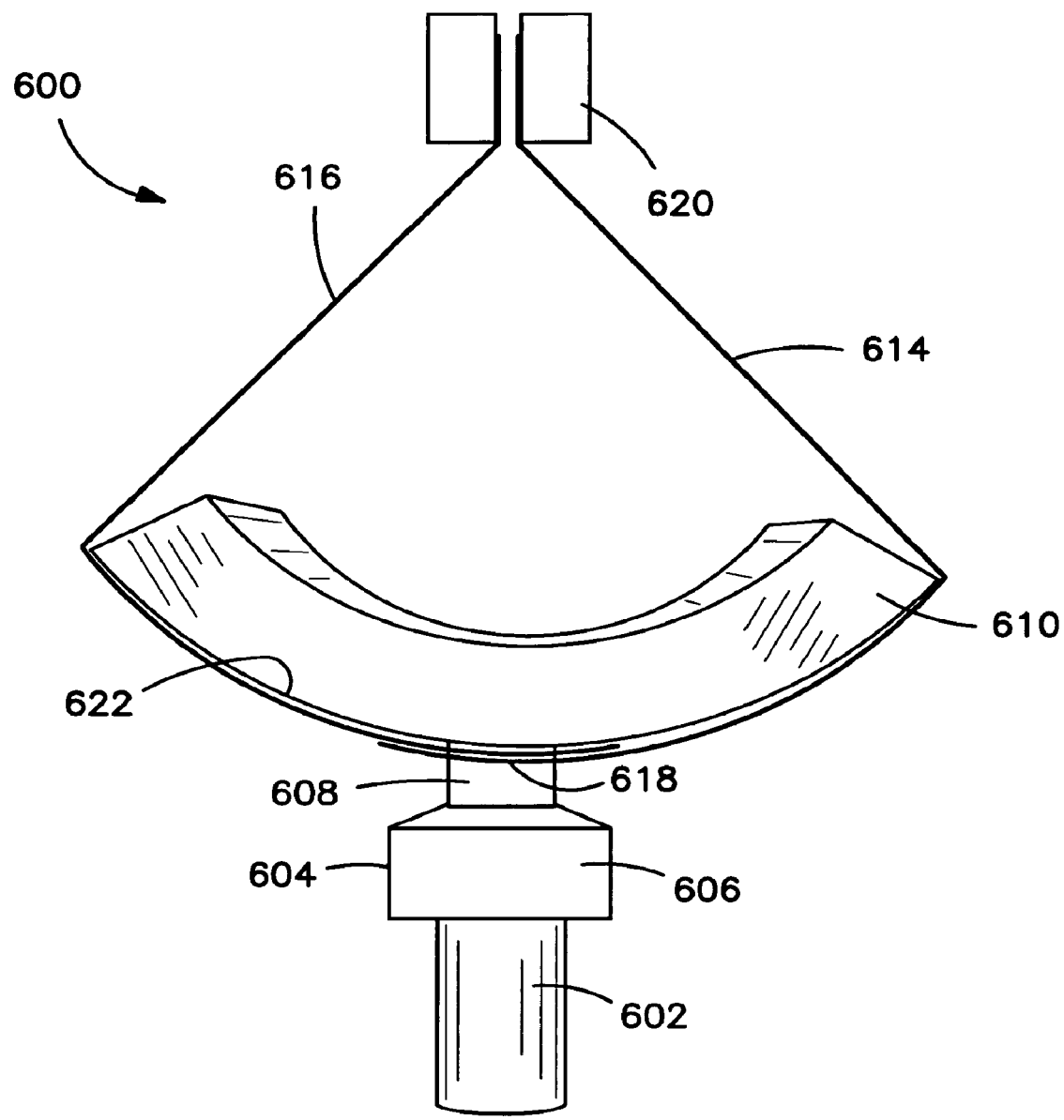
FIG. 12 shows another view of the apparatus used for the Curved Shear Attachment Strength test.

As shown in FIG. 10 and also in a side view in FIG. 12, the curved section 610 is used to hold a length of a two-inch wide foam layer strip 614 and a length of a three-inch wide landing layer strip 616 that overlap and are joined in an attachment zone 618 while the remote ends of the foam layer strip 614 and the landing layer strip 616 are also held in an upper clamp 620 connected to the movable head (not shown) of the universal testing machine (not shown). The foam layer and landing layer strips 614 and 616, respectively, are 9.5-inch long unless otherwise specified. The joining of the foam layer and landing layer strips 614 and 616, respectively, in the attachment zone 618 is carried out by superposing the laterally centered, aligned foam layer and landing layer strips 614 and 616, respectively, to from an overlap region 612 that is 1 inch long and 2 inches wide and then applying a load to ensure good contact. Unless otherwise specified, the load was provided by a brass laboratory roller having a mass of 7.0 kilograms, which was slowly rolled over the attachment zone 618 twice (forward and then back). After attaching the foam layer and landing layer strips 614 and 616, respectively, the attachment zone 618 is then centered on the lower portion of the curved section 610 and the ends of the foam layer and landing layer strips 614 and 616, respectively, remote from the attachment zone 618 are then placed in the jaw of the upper clamp 620. The lower surface of the upper clamp 620 is 3 inches above the upper surface of the curved section 610 before the test procedure begins. There is negligible tension yet no significant slack in the foam layer and landing layer strips 614 and 616, respectively, before the test procedure begins.

A measure of the strength of the attachment in the overlap region 612 may be obtained by running the universal test machine as if a tensile test were being carried out and measuring the peak load at failure. The test procedure is executed by moving the upper mount upwards at a crosshead speed of 10 inches per minute until there is failure, which may be failure of the attachment zone 618 or, in some cases, breaking of one of the foam layer and landing layer strips 614 and 616, respectively, elsewhere. The peak load before failure is the attachment strength.

Results of the increase in the attachment strength of the mechanical fastener are shown in Table 1.

TABLE 1

Effect of Surface Treatment with 85 Hook-Roller Method on Attachment Strength

| | Before treatment w/hook | | | | After treatment w/hook | | | | % |
|---|---|---|---|---|---|---|---|---|---|
| | Peak load, gf | | | Shear | Peak load, gf | | | Shear | |
| | AVG | STD | % COV | $g/in^2$ | AVG | STD | % COV | $g/in^2$ | Increase |
| Necked SMS | 659 | 206 | 39 | 329 | 1234 | 177 | 14 | 617 | 88 |
| SBL | 310 | 40 | 13 | 155 | 1223 | 185.3 | 15 | 612 | 295 |
| Necked spunbond | 352 | 149 | 42 | 176 | 436 | 181 | 42 | 218 | 24 |

EXAMPLE 2

Figure 13:
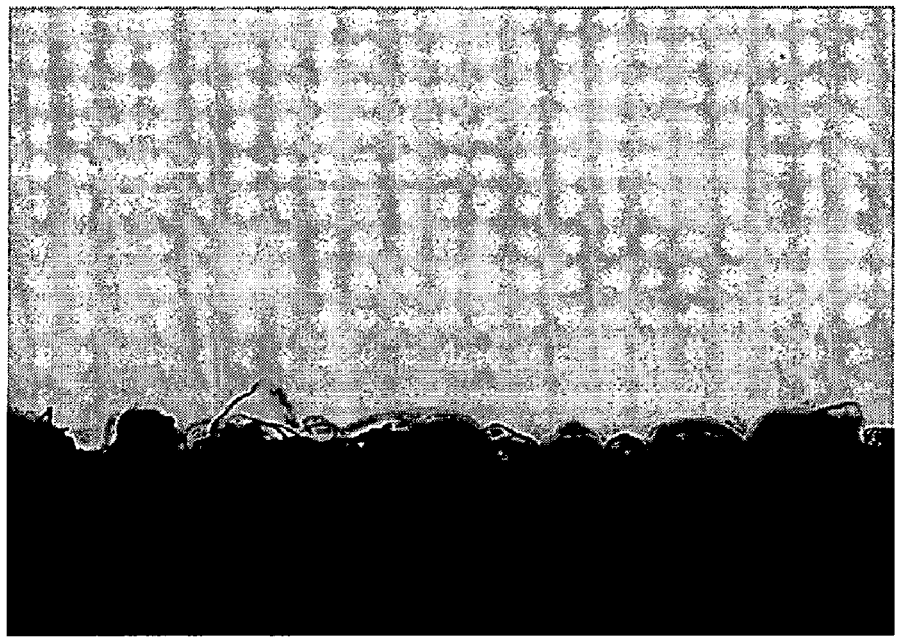
FIG. 13 is a side view of the surface of an exemplary engagement surface of an exemplary landing layer prior to treatment.
Figure 14:
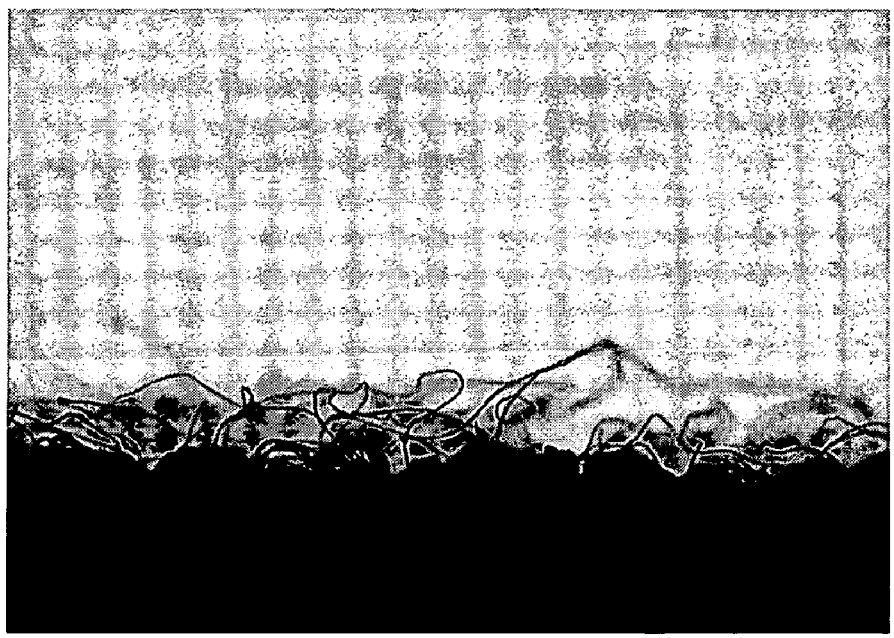
FIG. 14 is a side view of the exemplary engagement surface of the landing layer of FIG. 13.

In order to quantify the increase of surface fuzziness on the engaging surface of fibrous material achieved by the mechanical treatment described above, the method of measuring fuzz on edge was used. This method was disclosed previously in US Patent Application No. 2004/0229067 by Baggot et. al., filed on Jan. 7, 2004. A high-contrast imaging of fibrous materials both prior to and after the treatment was done according to this method. For example, FIG. 13 presents edge view of SBL material before treatment, while FIG. 14 presents edge view of SBL material after mechanical treatment done as described in Example 1. Quantification of perimeter/edge-length ratio (PR/EL) was also done as disclosed in more detail in US 2004/0229067.

Fuzz on edge measurements for the fibrous materials before (rows 1-3) and after (rows 4-6) mechanical treatment are presented in Table 2. Data listed are averages. PR/EL measurements indicated that differences existed between the materials before and after treatment. In addition to the PR/EL measurement, the number of fiber fragments per field-of-view (designated "# Fragments" in Table 2) also confirmed the differences when comparing materials before and after treatment.

TABLE 2

Fuzz-on-edge Measurements for Fibrous Materials

| No. | Sample ID | PR/EL | STD | # Fragments | STD | % Increase in PR/EL |
|---|---|---|---|---|---|---|
| 1 | Necked SB | 0.65 | 0.11 | 7.78 | 0.81 | — |
| 2 | Necked SMS | 1.39 | 0.42 | 14.25 | 3.61 | — |
| 3 | SBL | 2.68 | 0.30 | 32.02 | 3.33 | — |
| 4 | Mech. Treated Necked SB | 3.86 | 0.43 | 33.33 | 0.81 | 494 |
| 5 | Mech. Treated Necked SMS | 3.07 | 0.08 | 22.15 | 0.07 | 121 |
| 6 | Mech. Treated SBL | 7.17 | 0.32 | 68.98 | 3.43 | 167 |

The PR/EL data were attained by the using the following technique. A sample of the nonwoven was first prepared by cutting it into a strip that was approximately 20 cm in length. The width was approximately 4-5 cm. A fold was imparted along the length of the nonwoven strip by taping down one end onto a beveled piece of glass using a common, transparent tape (e.g., SCOTCH® Brand transparent tape sold by 3M Corp.) so that approximately half the width of the material hung over the beveled glass edge. The beveled edge was 3/32" in width. The sample was lightly stretched on the opposite end and then fastened down with another small piece of tape. The light stretching was done to remove any macro-wrinkles and puckers inherently present in the material. After taping down the entire long edge stretching between the two ends, the glass piece was inverted. The loose sample portion sticking out past the beveled edge was then gently pulled over the edge and taped onto the opposite side of the glass relative to the first sample edge. When taping down the second edge on the opposite glass surface, the material was again lightly stretched in an effort to remove any large wrinkles. Along the edge of the fold, twenty fields of view showing fibers that protrude from the surface of the material are then counted and their perimeter measured. The PR/EL value is the sum of the perimeters of the counted fibers divided by the length of the edge over which they were counted. Average PR/EL ratio and the number of fragment values that were acquired from samples 1-6 are shown in Table 2.

Figure 15:
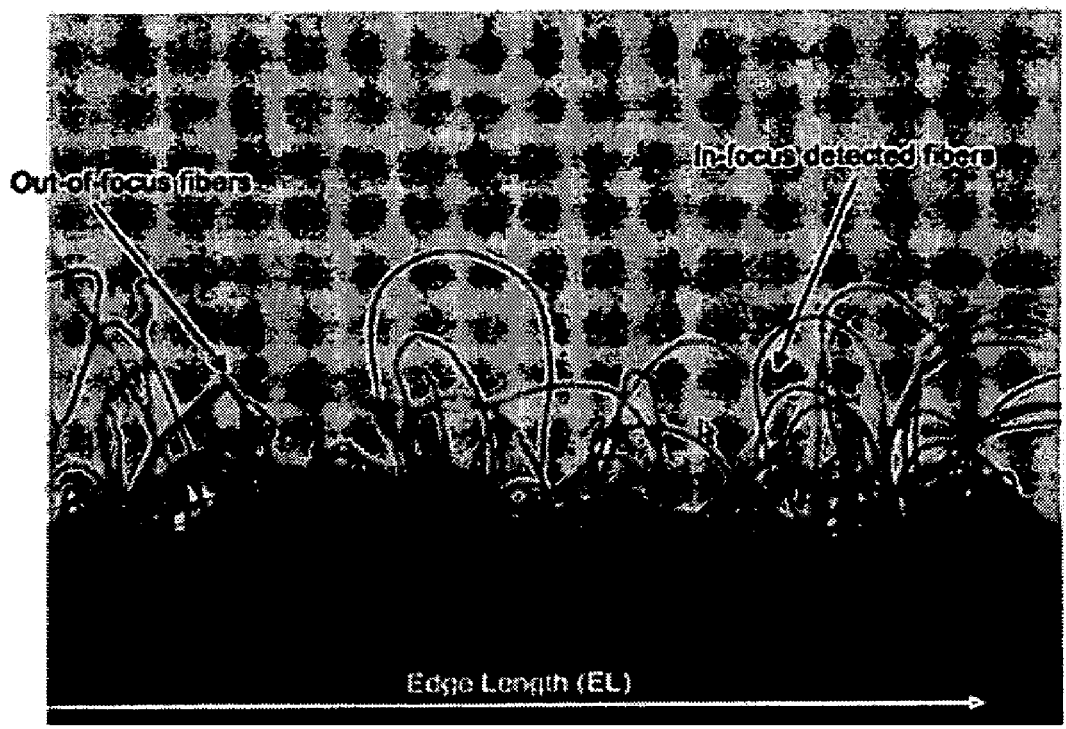
FIG. 15 is a close up view of the exemplary engagement surface of the landing layer of FIG. 14.

The PR/EL data were obtained using a Quantimet 600 Image Analysis System obtained from Leica of Deerfield, Ill. After a sample was prepared as previously described, it was then analyzed using the Quantimet 600 and the following software and equipment to determine the total circumference of the protruding fibers and the edge length of the nonwoven over which that total circumference was obtained. For example, referring to FIG. 15, the dark black area corresponds to the nonwoven that is folded over the beveled glass, the gray area is the background and in-focus fibers are the protruding fibers. Thus, the PR/EL is the accumulated perimeter of the in-focus fiber areas divided by the edge length (which as depicted in FIG. 15 would be the frame width of that figure). Approximately three nonwoven strips were analyzed per sample. The following software written in QUIPS language was on the Quantimet 600 to obtain PR/EL set forth herein.

QUIPS Routine FOE1

NAME=FOE1
PURPOSE=Measures Fuzz-on-edge properties of stretchable non-woven materials
CONDITIONS=SONY 3CCD (DXC-930P) vid.; 60-mm Micro-Nikkor (f/4) w/15 mm ext. tube (max. mag. for focus); Transmitted light through 4"×5" mask; DCI stage; beveled glass sample holders.
Open Files and Initial Variables
Open File (C:\EXCEL\DATA\FOE1.XLS, channel #1)
PERIM=0

PREL=0
TOTPREL=0
TOTFIELDS=0
MFLDIMAGE=0
FRAGMENTS=0
TOTFRAGMENTS=0
CALVALUE=8.23
Image and Frames Set-Up
Image frame (x 0, y 0, Width 736, Height 574)
Measure frame (x 32, y 61, Width 676, Height 512)
Calibrate (CALVALUE CALUNITS$ per pixel)
PauseText ("Set up sample and adjust white level to 1.00")
Image Setup [PAUSE] (Camera 5, Gain 74.99, Offset 74.99, Lamp 43.69)
Enter Results Header
File Results Header (channel #1)
File Line (channel #1)
Enter Sample Loop
Stage (Define Origin)
Stage (Scan Pattern, 20×1 fields, size 7299.804688×132400.937500)
For (FIELD=1 to FIELDS, step 1)
Image Acquire and Detect
Image Setup (Camera 5, Gain 74.99, Offset 74.99, Lamp 43.69)
Acquire (into Image0)
Detect (blacker than 127, from Image0 into Binary0 delineated
Image Processing
Binary Amend (Open from Binary0 to Binary1, cycles 9, operator Disc, edge erode on)
Binary Logical (C=A XOR B: C Binary2, A Binary0, B Binary1)
Binary Amend (Open from Binary2 to Binary3, cycles 1, operator Disc, edge erode on)
Field Measurements
MFLDIMAGE=3
Measure field (plane MFLDIMAGE, into FLDRESULTS (2))
Selected parameters: Area, Perimeter
PERIM=FLDRESULTS(2)
PREL=(PERIM)/(676*CALVALUE)
TOTPREL=TOTPREL+PREL
TOTFIELDS=TOTFIELDS+1
File (PREL, channel #1, 3 digits after '.')
Field Histogram #1 (Y Param Number, X Param PREL, from 0. to 20., linear, 20 bins)
Display Field Histogram Results (#1, horizontal, differential, bins+graph (Y axis linear), statistics)
Data Window (741, 553, 529, 467)
Feature Measurements
Measure feature (plane Binary3, 32 ferets, minimum area: 10, grey image: Image0)
Selected parameters: Area, X FCP, Y FCP, Perimeter
FRAGMENTS=Field Sum of (PACCEPTED(FTR))
File (FRAGMENTS, channel #1, 0 digits after '.')
TOTFRAGMENTS=TOTFRAGMENTS+FRAGMENTS
File Line (channel #1)
Stage (Step, Wait until stopped+550 msecs)
Next (FIELD)
Output
Set Print Position (8 mm, 8 mm)
Print Results Header
Print Line
Print ("Mean PR/EL=", no tab follows)
Print (TOTPREL/TOTFIELDS, 3 digits after '.', no tab follows)
Print Line
Print ("Total Fields=", no tab follows)
Print (TOTFIELDS, 0 digits after '.', no tab follows)
Print Line
Print ("Mean Fragments per Field=", no tab follows)
Print (TOTFRAGMENTS/TOTFIELDS, 2 digits after '.', no tab follows)
Print Line
Print Line
Print ("Count vs. PR/EL (mm/mm)", no tab follows)
Print Line
Print Field Histogram Results (#1, horizontal, differential, bins+graph (Y axis linear), statistics)
Set Image Position (left 98 mm, top 128 mm, right 183 mm, bottom 195 mm, Aspect=Image Window,
    Caption:Bottom Centre, "Example Image")
Grey Util (Print Image0)
Close File (channel #1)
END Equipment List IA System—Quantimet 600 (Leica, Inc., Cambridge, UK)
IA System Software—QWIN Version 1.06
Video Camera—SONY® Model DXC-930P (736×574 pixel resolution)
Camera Pole—Polaroid MP4 Land Camera
Lens—60-mm AF Micro Nikkor (Nikon Corp., Japan) w/15-mm extension tube
1:1 relay adaptor #C20047 (Century Optics, USA)
Auto-Stage—HM-1212 (Designed Components Incorporated, Franklin, Miss.)
Light Source—Chroma Pro 45 (Circle S, Inc., Tempe, Ark.)
Macro-viewer—Kreonite, Inc.

These and other modifications and variations to the present invention may be practiced by one of ordinary skill in the art, without departing from the spirit and scope of the present invention, which is more particularly set forth in the appended claims. In addition, it should be understood that aspects of the various embodiments may be interchanged, both in whole or in part. Furthermore, those of ordinary skill in the art will appreciate that the forgoing description is by way of example only, and is not intended to limit the invention so further described in the appended claims.

What is claimed:

1. A method of increasing a perimeter/edge-length ratio of a landing layer of a mechanical fastener, comprising:
    providing a mechanical fastener comprising a foam layer and a landing layer, wherein the landing layer comprises a fibrous web defining an engaging surface, wherein said engaging surface of the fibrous web landing layer has an original perimeter/edge-length ratio; and
    mechanically modifying the engaging surface of the landing layer such that the engaging surface has an improved perimeter/edge-length ratio that is at least about 50% higher than the original perimeter/edge-length ratio.

2. A method as in claim 1, wherein the improved perimeter/edge-length ratio is at least about 75% higher than the original perimeter/edge-length ratio.

3. A method as in claim 1, wherein the improved perimeter/edge-length ratio is at least about 100% greater than the original perimeter/edge-length ratio.

4. A method as in claim 1, wherein the landing layer comprises a nonwoven fibrous web.

5. A method as in claim 4, wherein the landing layer comprises a spunbond web.

6. A method as in claim 4, wherein the landing layer comprises a bonded carded web.

7. A method as in claim 4, wherein the landing layer comprises a meltblown web.

8. A method as in claim 1, wherein the perimeter/edge-length ratio of the engaging surface is increased by a process selected from the group consisting of brushing, napping, necking in the cross-machine direction, stretching in the machine direction, needle punching, hydroentangling, dragging over an edge, and dragging over an ultrasonic horn.

* * * * *

UNITED STATES PATENT AND TRADEMARK OFFICE
CERTIFICATE OF CORRECTION

PATENT NO. : 7,640,637 B2 Page 1 of 1
APPLICATION NO. : 11/264818
DATED : January 5, 2010
INVENTOR(S) : Efremova et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 865 days.

Signed and Sealed this

Sixteenth Day of November, 2010

David J. Kappos
*Director of the United States Patent and Trademark Office*